(12) United States Patent
Soller et al.

(10) Patent No.: US 6,406,673 B1
(45) Date of Patent: Jun. 18, 2002

(54) VOLATILE DISPENSER LAMP

(75) Inventors: Douglas A. Soller; Pamela J. Taylor, both of Mt. Pleasant, WI (US)

(73) Assignee: S.C. Johnson & Son, Inc., Racine, WI (US)

(*) Notice: Subject to any disclaimer, the term of this patent is extended or adjusted under 35 U.S.C. 154(b) by 0 days.

(21) Appl. No.: 09/952,470

(22) Filed: Sep. 14, 2001

(51) Int. Cl.⁷ .................................................. A61L 9/02
(52) U.S. Cl. ........................... 422/126; 43/125; 43/129; 422/125
(58) Field of Search .................................. 422/126, 125, 422/4, 5; 431/344; 43/1, 124–129

(56) References Cited

U.S. PATENT DOCUMENTS

| | | |
|---|---|---|
| 692,075 A | 1/1902 | Searle |
| 4,321,656 A | 3/1982 | Graver, Jr. |
| 5,359,801 A | 11/1994 | Mattucci et al. |
| 5,700,430 A | 12/1997 | Bonnema et al. |
| 5,744,106 A | 4/1998 | Eagle |
| 5,928,605 A | 7/1999 | Bonnema et al. |
| 6,033,212 A | 3/2000 | Bonnema et al. |
| 6,061,950 A | 5/2000 | Cary et al. |

FOREIGN PATENT DOCUMENTS

WO    WO 00/78135    12/2000

*Primary Examiner*—Robert J. Warden, Sr.
*Assistant Examiner*—Sean E. Conley

(57) ABSTRACT

A combination lamp and volatile dispenser provides light and dispenses a volatile material such as an insecticide from a burnable coil. There is a burn vessel, a flame source and a chimney. The burn vessel houses the coil, has openings allowing air to pass through the burn vessel, and supports the chimney and flame source. The arrangement allows volatiles released from the burning coil in the vessel to be drawn to the outside air through the chimney. A kit for replacing the candle and coil consumed during use is also disclosed, as are methods of use of such lamps.

13 Claims, 3 Drawing Sheets

VOLATILE DISPENSER LAMP

CROSS-REFERENCE TO RELATED APPLICATIONS

Not applicable.

STATEMENT REGARDING FEDERALLY SPONSORED RESEARCH/DEVELOPMENT

Not applicable.

BACKGROUND OF THE INVENTION

This invention relates to dispensers for volatile materials such as insect control agents, scents and the like. In particular, the invention relates to dispensers that simultaneously dispense a volatile from a burnable coil and provide illumination.

There are a number of known dispensers for volatile ingredients that provide the additional feature of lighting the surrounding area. This is particularly desirable for environments such as camping and picknicking areas.

U.S. Pat. No. 6,033,212 discloses a lantern that burns fuel for light. The flame is contained in a glass, transparent globe that is covered at its top. The cover has a slot that receives a pad impregnated with a volatile material having an insect control agent. The waste heat from the burning fuel exits the globe through the slot, which heats the pad and releases the volatile. WO 00/78135 is another example of mounting a pad adjacent a flame. However, the types of pads used with these designs can be somewhat costly to produce, and in some cases place constraints on the performance of the active.

Citronella candles also provide light and also disperse an insect repellent. Unfortunately, exposed candle flames can be snuffed by the wind.

Insect coils are also well known. They are typically a spiral coil of compressed, largely pulp material which typically has been impregnated with an insect control active. The coils can alternatively or in addition contain other active ingredients having different characteristics, such as aromatics or disinfectants. These coils are extremely inexpensive, and due to their slow burn rate can provide overnight protection.

However, these coils can also snuff out if exposed to too much wind. Thus, it has been proposed to house them in special pots that restrict outside gusts from reaching the coil. This also has the benefit of inhibiting persons from accidently touching the coil while it is burning. See e.g. U.S. Pat. No. 6,061,950. However, these pots may disperse active at a somewhat slower rate, thus requiring them to be started a longer time before an area is deemed "mosquito safe".

Thus, there still is a need for an improved volatile dispensing device.

SUMMARY OF THE INVENTION

In one aspect the invention provides a lamp for dispensing a volatile material. There is a burnable coil having the volatile material, and a burn vessel for housing the coil. The vessel has openings allowing air to pass through the vessel and by the coil. A flame source is mounted above the coil. A chimney is mounted around the flame source so as to direct volatized material from the burning coil to be drawn into the chimney past the flame source and then up outside the chimney.

In preferred forms the burn vessel has a cover and a base. The base has a raised support for supporting the coil above a bottom of the base. The chimney is removably seated on the cover in a recess in the cover. The cover further includes a plurality of openings, some of which are positioned radially inside, and some of which are positioned radially outside, of the recess.

The cover recess can include a central depression for receiving the flame source such as a candle. The flame source can have a cup containing the candle, where the cup has a bottom with a recess sized to receive an upwardly extending mounting post of the cover. The base can have peripheral walls with a plurality of openings therein.

In another aspect, the invention provides a kit providing a replacement coil and candle for lamps of the above kind.

Still another aspect of the invention provides a method for controlling flying insects. One provides the above lamp, lights both the coil and the flame source, and permits volatizable material such as an insect control agent to pass from the coil, past the flame, and out an upper opening of the chimney so as to expose an area to the volatizable material.

In an especially preferred form the lamp is used to repel and/or kill insects using an insect control agent such as an insecticide, a repellent, or an insect growth regulator. A wide variety of insect control agents are known which can be used for this purpose (e.g. those which have previously been incorporated into mosquito coils). We prefer d-cis/trans allethrin for use in mosquito control in the context of this lamp.

Because the lamp provides both light and insect control, and does so even in windy environments, it is particularly suitable for use when camping, or when eating in a backyard environment around sunset. The device is designed to utilize extremely inexpensive consumables (e.g. standard conventional burnable coils; standard wax candles).

The flame source serves multiple purposes. It provides light, while also creating convection to draw outside air past the burning coil. The air/volatile mix is then propelled out the top of the chimney to widely and quickly disperse the active.

The foregoing and other advantages of the present invention will appear from the following description. In the description, reference is made to the accompanying drawings which form a part hereof and in which there is shown by way of illustration preferred embodiments of the invention. These embodiments do not represent the full scope of the invention. Rather, reference should be made to the claims for interpreting the full scope of the invention.

DETAILED DESCRIPTION OF THE PREFERRED EMBODIMENTS

Figure 1:
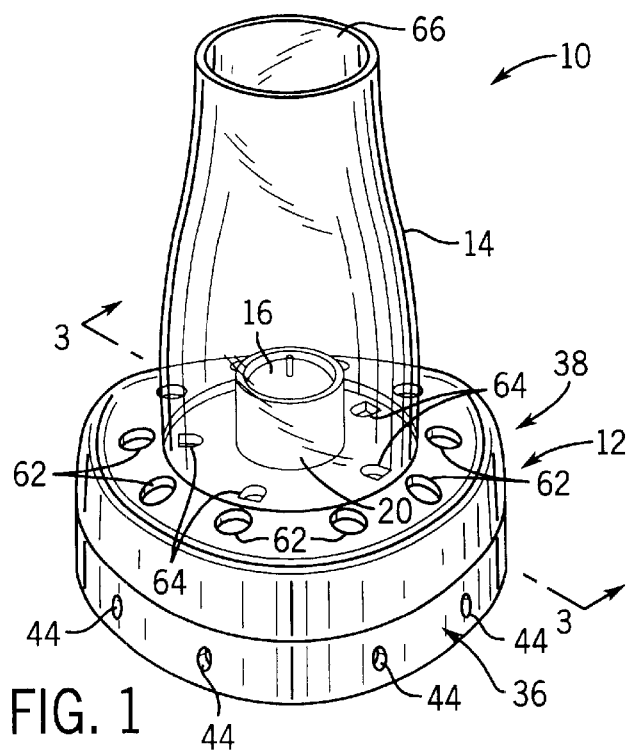
FIG. 1 is a perspective view of a volatile dispenser lamp of the present invention.

A lamp 10 includes a burn vessel 12 supporting an open-ended chimney 14 and a candle 16. The burn vessel 12 houses a burnable coil 18 and thus is preferably made of a suitable heat resistant material, such as ceramic. The chimney 14 can be made of glass or a heat-resistive plastic such as a V-O flame rated polycarbonate (commercially available under the name "Makrolon® 6455" from Bayer Corporation). Preferably, the chimney 14 is translucent to allow light to pass out but to somewhat obscure the view inside the chimney 14. However, it could also be transparent.

The burnable coil 18 has a spiral configuration and is otherwise of the type disclosed in U.S. Pat. No. 6,061,950 (e.g. see U.S. Pat. No. 5,657,574).

Figure 3:
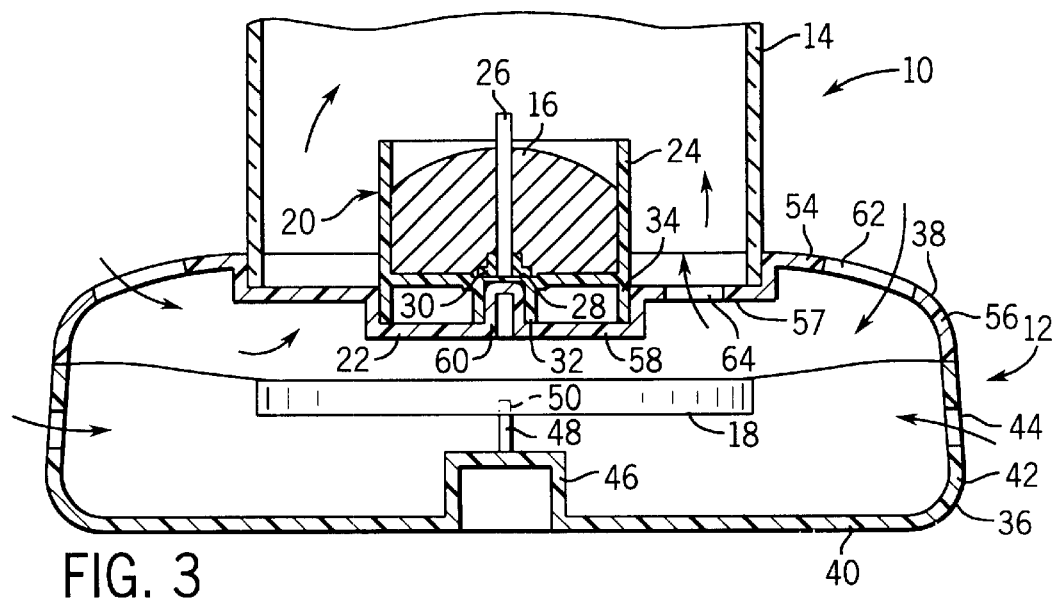
FIG. 3 is a partial cross-section through line 3—3 of FIG. 3.
Figure 2:
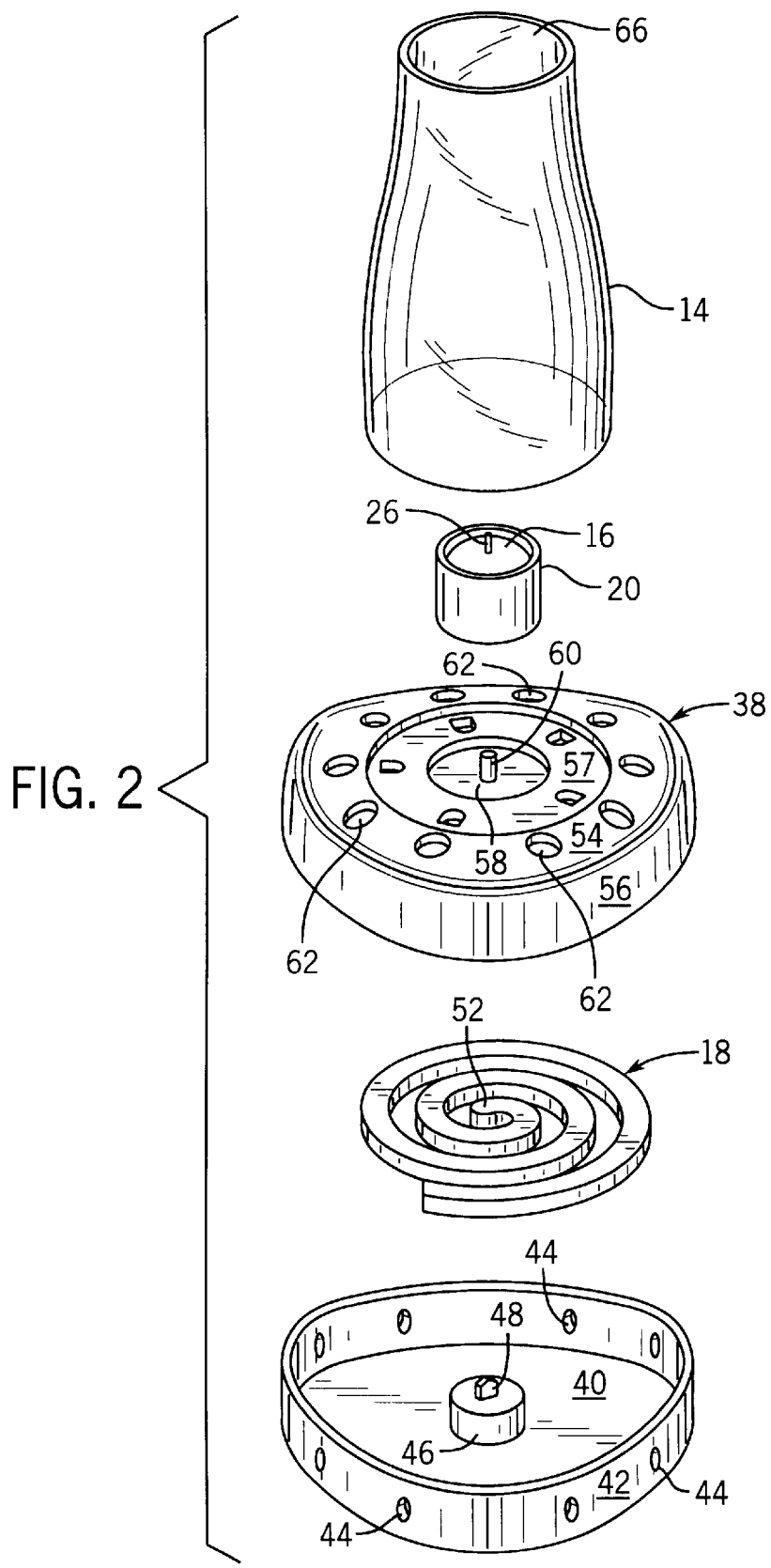
FIG. 2 is an exploded perspective view thereof.
Figure 4:
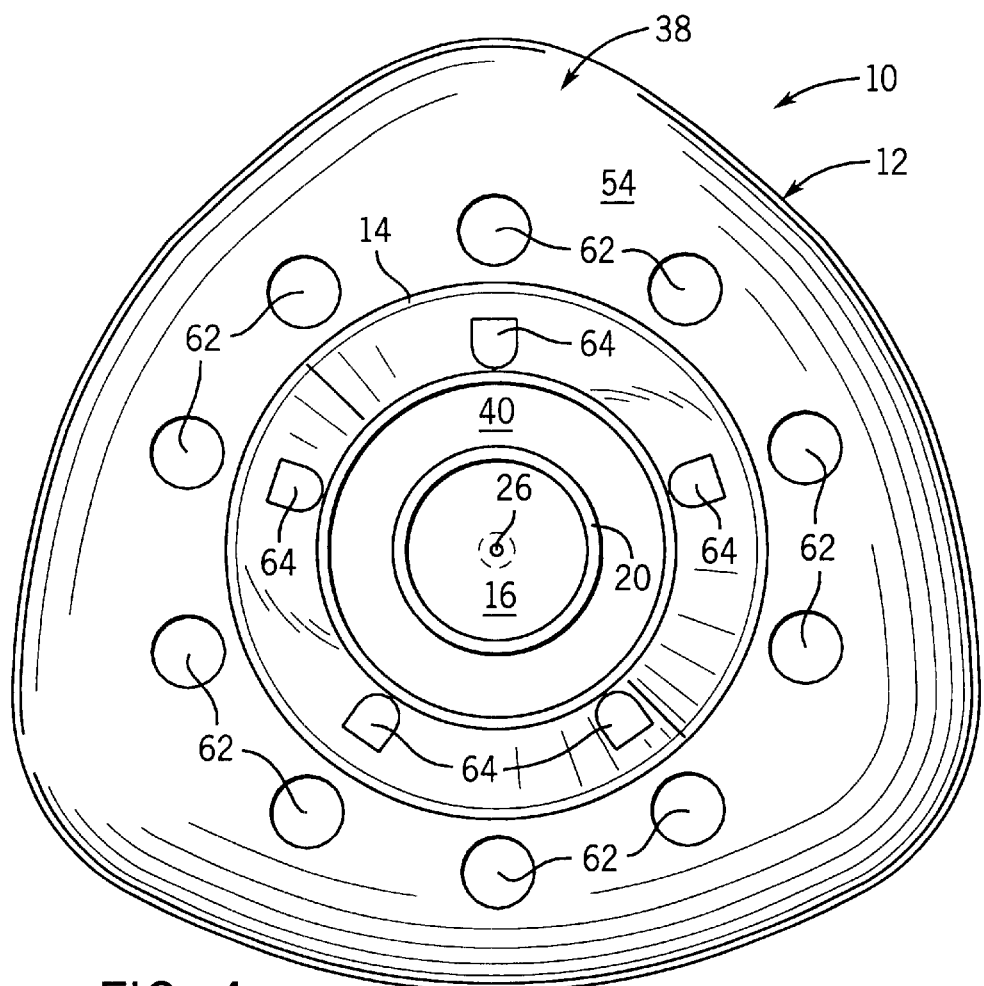
FIG. 4 is a top view thereof.

Referring to FIG. 3, the candle 16 is contained in a cup 20 having a floor 22 and a cylindrical wall 24 defining an open top. The cup 20 is preferably made of a V-O flame rated polycarbonate material. The candle 16 is preferably a conventional cylindrical paraffin wax candle having a wick 26 held at the bottom by a wick clip 28 disposed in a depression 30 in floor 22 to restrict movement. Alternatively, the flame source could provide an oil or gas flame, with a suitable container for each.

A cylindrical socket 32 extends downwardly from the center of the cup floor 22 as does a cylindrical support member 34 at the periphery of the cup floor 22.

The support member 34 is at least as tall as the socket 32 to allow the candle cup 20 to sit upright on top of the burn vessel 12.

The burn vessel 12 includes a base 36 and a cover 38. The base 36 may be circular, or as shown in the drawings be contoured triangular in top view. Bottom 40 has upright walls 42 extending around its periphery having spaced openings 44 there through. The bottom 40 also has a raised coil support 46 at its center with an upwardly extending spade 48. The spade 48 is sized to fit in a recess 50 in a mounting end 52 of the coil 18. The coil support 46 thus supports the coil 18 spaced off the bottom 40 (to reduce the occurrence of a burning coil 18 being inadvertently snuffed out during use).

The cover 38 has a top 54 with downwardly extending peripheral walls 56 sized and configured to sit on (or alternatively) mate with the walls 42 of the base 36. The top 54 is formed with a central recess 57 sized to receive the bottom edge of the chimney 14. At the center of the recess 57 is an additional depression 58 for receiving the candle cup 20. At the center of the depression 58 is an upwardly extending mounting post 60 for engaging the cup socket 32. This engagement is designed to grip the candle cup 20 to the cover 38 so that the candle 16 will not be tipped if the chimney 14 is inadvertently knocked off the burn vessel 12.

The cover 38 has a plurality of outer openings 62 spaced around the recess 57 through the top 54 and a plurality of inner openings 64 spaced around the depression 58 through the recess 57. Thus, the outer openings 62 are open to the outside air and the inner openings 64 are at the interior of the chimney 14. Both are in communication with the interior of the burn vessel 12.

When the candle 16 is lit and the chimney 14 is place on the burn vessel 12, the heat from the candle 16 creates a convective air flow which pulls air in through the openings in the base 36 past burning coil 18. The air stream picks up the released volatile material. The air stream then is drawn through the inner openings 64 of the cover 38 around the candle 16 and up into the chimney 14. The air stream exits the chimney 14 through an upper opening 66 allowing the volatile material to reach the surrounding outside air.

The air coming into the burn vessel 12 is cool relative to the air above and surrounding the open flame of the candle 16, as is the air in the burn vessel 12 due to the no-flame burn of the coil 18. Thus, the candle 16 and the chimney 14 are ventilated and cooled by the air flow from below. In fact, the coolest air tends to form at the outer periphery of the air flow adjacent wall of the chimney 14 and around the hotter air flow at the center of the chimney 14 above the candle 16. This air flow pattern maintains the chimney 14 at a cooler temperature, while focusing a higher heat at the center of the area extending up through the top of the chimney 14. This helps to preserve the integrity of the chimney 14 and make it cooler to the touch (while at the same time establishing a hot area for expelling the volatile material emanating from the coil 18).

The invention thus provides a device particularly suited for outdoor use. The device utilizes conventional burnable coils impregnated with insect control volatiles that are released when the coil is burnt. A candle or other flame source provides light. The dispersal rate for the active is significantly higher than for a mosquito coil mounted in a conventional pot, thus permitting an area to be rendered safer for use without mosquito problems at a sooner time. At the same time, the snuffing potential due to outside wind gusts is very low.

The invention also provides a kit for replacing the consumable items (i.e., the candle and the coil).

The candle is preferably made of paraffin wax by a process of bonding small wax granules in a compression mold. This technique is well known for producing candles with consistent dimensions and densities. The preferred candle weighs from 15 to 20 grams with a diameter of about 37 mm and has an overall height of about 20 mm at its center.

The preferred coil is as described above. The coil preferably has a burn rate allowing the impregnated volatile ingredients to be exhausted substantially at the same time that the candle is exhausted. Suitable volatile ingredients include (without limitation) insect control actives, aromatics and other air quality modifying materials.

Exhausted coils are replaced by separating the cover from the base, removing any remaining non-burnt section of the coil, emptying the ash, and attaching the mounting end of the replacement coil from the kit to the spade of the coil support. Exhausted candles are replaced by lifting the chimney from the cover, removing the old candle cup and attaching the replacement candle from the kit to the cover by pressing the socket onto the mounting post. The interfitting of the candle and post is a safety feature insuring that the candle will be stably held The coils can be lit from their outer edge with a match, followed by closing the burn vessel, mounting the candle, lighting the candle, and mounting the chimney on the cover. The device can either be allowed to burn until exhausted, or one can blow the flame out and manually snuff out the coil.

Preferred embodiments of the invention have been described in detail for the purpose of disclosing a practical, operative structure whereby the invention may be practiced advantageously. These designs are intended to be illustrative, and not exhaustive. For example, while the dispenser is shown and described for use with an insect control active, it could instead be used to dispense aromatics, disinfectants or other volatiles. Thus, the claims should be looked to in order to assess the full scope of the invention.

INDUSTRIAL APPLICABILITY

The present invention provides an apparatus providing illumination and dispensing volatiles useful, among other things, to repel insects.

We claim:

1. A lamp for dispensing a volatile material, comprising:

a burnable coil having a volatile material;

a burn vessel for housing the coil, the vessel having openings allowing air to pass through the vessel and by the coil;

a flame source mounted above the coil; and a chimney mounted around the flame source allowing volatized material from the burning coil to be drawn into the chimney, past the flame source and then outside the chimney.

2. The lamp of claim 1, wherein the burn vessel has a cover and a base.

3. The lamp of claim 2, wherein the base has a raised support for supporting the coil above a bottom of the base.

4. The lamp of claim 2, wherein the chimney is removably seated on the cover.

5. The lamp of claim 4, wherein the cover has a recess for receiving the chimney.

6. The lamp of claim 5, wherein the cover further includes a plurality of openings positioned radially outside of the recess.

7. The lamp of claim 5, wherein the cover further includes a plurality of openings positioned radially inside of the recess.

8. The lamp of claim 5, wherein the recess includes a central depression for receiving the flame source.

9. The lamp of claim 1, wherein the flame source is a candle.

10. The lamp of claim 2, wherein the flame source comprises a cup containing the candle, the cup having a bottom with a recess sized to receive an upwardly extending mounting post of the cover.

11. The lamp of claim 2, wherein the base has peripheral walls with a plurality of openings therein.

12. A kit suitable to replace the coil and candle of a lamp of claim 1, comprising:

a burnable coil impregnated with an insect control agent; and a candle.

13. A method for controlling flying insects, comprising:

providing a lamp of claim 1;

lighting the coil and the flame source; and permitting volatizable material to pass from the coil, past the flame, and out an upper opening of the chimney so as to expose an area to the volatizable material;

wherein the volatizable material is an insect control agent.

* * * * *